United States Patent [19]

Rusch

[11] Patent Number: 4,824,467

[45] Date of Patent: Apr. 25, 1989

[54] COMPOSITION FOR DEFOLIATION OF PLANTS

[75] Inventor: Reinhart Rusch, D-1000 Berlin 28, Fed. Rep. of Germany

[73] Assignee: Schering Aktiengesellschaft, Fed. Rep. of Germany

[21] Appl. No.: 135,065

[22] Filed: Dec. 18, 1987

[30] Foreign Application Priority Data

Dec. 18, 1986 [DE] Fed. Rep. of Germany ....... 3643654
Dec. 18, 1986 [DE] Fed. Rep. of Germany ....... 3643655

[51] Int. Cl.⁴ .............................................. A01N 43/78
[52] U.S. Cl. .................................... 71/73; 71/DIG. 1; 71/74
[58] Field of Search ........................ 71/73, DIG. 1, 74

[56] References Cited

U.S. PATENT DOCUMENTS 4,461,638 7/1984 Rajadhyaksha ................... 71/27
4,613,354 9/1986 Rusch ..................................... 71/73

FOREIGN PATENT DOCUMENTS 0077078 4/1983 European Pat. Off. .

Primary Examiner—Catherine L. Mills
Attorney, Agent, or Firm—Ostrolenk, Faber, Gerb & Soffen

[57] ABSTRACT

The invention relates to a new composition for defoliation of plants with synergistic activity, containing a mixture of 1-phenyl-3-(1,2,3-thiadiazol-5-yl)urea and 1-dodecylazacycloheptan-2-one or a mixture of 1-phenyl-3-(1,2,3-thiadiazol-5-yl)urea, 1-dodecylazacycloheptan-2-one and 3-(3,4-dichlorophenyl)-1,1-dimethylurea and its use especially for the defoliation of cotton plants.

11 Claims, No Drawings

COMPOSITION FOR DEFOLIATION OF PLANTS

This invention relates to a new composition for defoliation of plants having synergistic activity which contains as the active ingredients a mixture of 1-phenyl-3-(1,2,3-thiadizol-5-yl)urea and 1-dodecylazacycloheptan-2-one or a mixture of 1-phenyl-3-(1,2,3-thiadiazol-5-yl)urea, 1-dodecylazacycloheptan-2-one and 3-(3,4-dichlorophenyl)-1,1-dimethylurea.

The composition consists essentially of two and/or three components that mutually affect each other when used together and display a biological activity which is greater than the sum of the activities used alone and shows an effect which can be described as synergistic. This synergistic activity introduces in the present case the increased formation of separating tissue in plants and thus leads to a controlled removal of the leaf stalk and leaves of the treated plants.

1-Phenyl-3-(1,2,3-thiadizol-5-yl)urea is already known as a plant defoliant (DE-OS No. 25 06 690).

1-Dodecylazacycloheptan-2-one is also known and have been described, inter alia, as agents for enhancing the penetration of pesticides and nutrients into plants. (EP 77 078 and EP 160 111). However, its use as a defoliant or as a synergist for defoliants is not known.

3-(3,4-Dichlorophenyl)-1,1-dimethyl urea is generally known, under the common name diuron, as a herbicide (USP 2 655 445).

Also mixtures with 1-phenyl-3-(1,2,3-thiadiazol-5-yl)urea for the defoliation of plants which show a synergistic activity, are already known (DE-OS No. 26 46 712 and DE-OS No. 32 22 622).

However, there still exists to an ever increasing extent a considerable requirement for further materials in this area with increased activity and with it the possibility of lower amounts of active material and especially an increasing demand for corresponding protection of the environment.

With the substances known up until now, clear progress has been made. However, it is not always satisfactory, especially when for acceptable activity at lower temperatures, higher rates of use are required, or for an acceptable activity also, the high rates of use are no longer allowed.

The object of the present invention is therefore to provide a composition for defoliation of plants having synergistic activity which does not have the drawbacks of the known substances.

This object can be solved according to invention by a composition which is characterised by comprising a mixture of the components
(A) 1-phenyl-3-(1,2,3-thiadiazol-5-yl)urea and
(B) 1-dodecylazacycloheptan-2-one
or
(A) 1-phenyl-3-(1,2,3-thiadiazol-5-yl)urea,
(B) 1-dodecylazacycloheptan-2-one and
(C) 3-(3,4-dichlorophenyl)-1,1-dimethylurea.

Surprisingly, the composition of the invention shows a defoliation activity that is often much greater than the sum of the activities of the single components when used alone, which is not predictable from the present state of knowledge.

The state of the art is considerably improved by the provision of the compositions of the invention.

This is demonstrated particularly in comparison with common defoliants, such as S,S,S-tributyl phosphorotrithioate or sodium chlorate, where addition of 1-dodecylazacycloheptan-2-one gives no increase in activity as is observed with the composition of the invention.

The composition of the invention is particularly valuable under climatic conditions where a single component alone does not produce clear defoliation.

The synergistic activity of the mixture of the invention is displayed when it contains to each part by weight of component A, 1 to 100 parts by weight of component B and 0 to 10 parts by weight of component C, but these limiting values can also be exceeded by larger or smaller amounts.

Optimal increase in activity is exhibited by the mixtures of the invention that contain for each part by weight of defoliant substance A, 1 to 50 parts by weight of component B and 0 to 5 parts by weight of component C. However, the proportion by weight depends on the sensitivity and resistivity of the plants, the time of use, the climatic conditions and the soil conditions.

The composition of the invention is suitable for the defoliation, and with it the facilitating of harvesting, of many plants, especially cotton.

The rates of use are as a rule in the range 1 to 10,000 grams of the mixture (components A, B and C) per hectare, especially 100 to 2000 grams of mixture per hectare.

The composition can be applied in customary fashion, for example with water as the carrier in spray mixture volumes of approximately 100 to 2000 l/ha. The composition can be applied using low-volume or ultra-low-volume techniques.

The composition of the invention can, if desired, be used in mixture with other active ingredients, for example defoliants, plant protection or pesticide materials depending on the desired object.

An increase in the activity and the speed of activity can also be obtained for example through use of additives which will increase the activity, such as for example, solvents, surfactants and oils. These can lead to a further reduction of the rates of use of the actual active ingredients.

The mixtures of the invention can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, as well as cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The content of the mixture (components A, B and C) in the various preparations can vary within wide limits. For example, the compositions can contain about 5 to 95 percent by weight of components A, B and C, and about 95 to 5 percent by weight liquid or solid carriers, as well as, optionally up to 30 percent by weight of surfactant.

Formulations can be prepared, for example, from the following ingredients.

(a)

95 percent by weight components A and B or A, B and C
5 percent by weight of a surfactant based on the polyoxyethylene derivative of sorbitan acid (b)

35 percent by weight components A and B
40 percent by weight colloidal silicic acid
10 percent by weight kaolin
10 percent by weight calcium lignosulphonate
2 percent by weight ammonium chloride
2 percent by weight of a surfactant based on polyoxyethylene derivatives
1 percent by weight of a surfactant based on dialkyl-naphthalensulphonate (c)

5 percent by weight components A and B
80 percent by weight bentonite
10 percent by weight calcium lignosulphonate
5 percent by weight of a surfactant based on fatty acid condensation products (d)

72 percent by weight components A, B and C
28 percent by weight of a surfactant based on ethoxylated tert alkylamine (e)

55 percent by weight components A, B and C
38 percent by weight colloidal silicic acid
5 percent by weight calcium lignosulphonate
2 percent by weight of a surfactant based on polyoxyethylene derivatives With unfavourable conditions for the defoliation, glasshouse tests are the basis for the following examples which as a general rule are carried out on cotton plants with 4 to 8 true leaves. The composition is applied in the form of suspensions or emulsions at a rate of 200 liters of water per hectare.

The evaluation of the experiment is carried out by counting the number of discharged leaves after the application and by estimation of the percentage of the total number of leaves. For each experimental member there is always present in each single experiment the same number of plants and leaves. From experiment to experiment the number of leaves for each experimental member did not vary and lay between 20 and 32 leaves.

The following reports of the experiment contain data about the components A, B and C, rates of use, as well as the calculation of the percentage rate of defoliation. Next to the percentage rate of defoliation obtained is given, in brackets, the value that would be expected for additive activity as calculated by the method of S. R. Colby (S R Colby "Calculating Synergistic and Antagonistic Responses of Herbicide Combinations", Weeds 15/1 (1967) pages 20 to 22).

The calculation was carried out according to the following equation:

$$E = X + Y + Z - \frac{(XY + XZ + YZ)}{100} + \frac{XYZ}{10000}$$

in wich
X = percentage defoliation with substance A at p kg/ha
Y = percentage defoliation with substance B azt q kg/ha
Z = percentage defoliation with substance C at r kg/ha
E = the expected defoliation by additive activity of the substances A+B+C at p+q+r kg/ha.

If the observed value is higher than that value E calculated according to Colby, the combination has synergistic activity.

EXAMPLE 1

Young cotton plants in the 5 to 6 leaf stage were treated with the active ingredients given below (repeated 4 times). The volume of water used was 200 l/ha.

After 2 weeks the percentage of discharged leaves was ascertained. The results are given in the following table.

| Components of invention | | Rate in g/ha | Defoliation (%) | E (according to Colby) |
|---|---|---|---|---|
| 1-Phenyl-3-(1,2,3-thiadiazol-5-yl)-urea | A | 20 | 10 | |
| | | 40 | 24 | |
| | | 80 | 40 | |
| 1-dodecylaza-cycloheptan-2-one | B | 240 | 0 | |
| | | 500 | 0 | |
| | | 1000 | 0 | |
| | | 2000 | 0 | |
| | A + B | 40 + 500 | 90 | (24) |

EXAMPLE 2

Young cotton plants in the 5 to 6 leaf stage were treated as in Example 1 and evaluated after 20 days at 15° to 17° C.

| Components of invention | | Rate in g/ha | Defoliation (%) | E (according to Colby) |
|---|---|---|---|---|
| 1-Phenyl-3-(1,2,3-thiadiazol-5-yl)-urea | A | 20 | 0 | |
| | | 40 | 0 | |
| | | 80 | 10 | |
| 1-dodecylaza-cycloheptan-2-one | B | 500 | 0 | |
| | | 1000 | 0 | |
| | A + B | 20 + 500 | 70 | (0) |
| | | 40 + 500 | 100 | (0) |

EXAMPLE 3

Young cotton plants in the 5 to 6 leaf stage were treated as in Example 2 and evaluated after 20 days at unfavorable temperatures (mainly between 15° and 20° C.).

| Components of invention | | Rate in g/ha | Defoliation (%) | E (according to Colby) |
|---|---|---|---|---|
| 1-Phenyl-3-(1,2,3-thiadiazol-5-yl)-urea | A | 50 | 10 | |
| | | 100 | 14 | |
| 1-dodecylaza-cycloheptan-2-one | B | 50 | 0 | |
| | | 100 | 0 | |
| | A + B | 50 + 50 | 38 | (0) |

EXAMPLE 4

Young cotton plants in the 5 to 6 leaf stage were treated as in Example 2 and evaluated after 13 days at unfavorable temperatures (mainly between 13° and 20° C.).

| Components of invention | | Rate in g/ha | Defoliation (%) | E (according to Colby) |
|---|---|---|---|---|
| 1-Phenyl-3-(1,2,3-thiadiazol-5-yl)-urea | A | 30 | 0 | |
| | | 60 | 0 | |
| 1-dodecylaza-cycloheptan-2-one | B | 500 | 0 | |
| | | 2000 | 0 | |
| | A + B | 30 + 500 | 85 | (0) |
| | A + B | 60 + 500 | 100 | (0) |
| Comparison | | | | |
| S,S,S—tributylphos-phosphorothioate | D | 350 | 65 | |
| | | 700 | 78 | |
| | B + D | 500 + 350 | 62 | (65) |
| | | 500 + 700 | 76 | (78) |
| Sodium chlorate | E | 1000 | 5 | |
| | B + E | 500 + 1000 | 5 | (5) |

EXAMPLE 5

Young cotton plants in the 5 to 6 leaf stage were treated with the active ingredients given below (repeated 4 times). The volume of water used was 200 l/ha.

After 2 weeks at 15° to 17° C. the percentage of discharged leaves was ascertained. The results are given in the following table.

| Components of invention | | Rate in g/ha | Defoliation (%) | E (according to Colby) |
|---|---|---|---|---|
| 1-Phenyl-3-(1,2,3-thiadiazol-5-yl)-urea | A | 25 | 0 | |
| | | 50 | 10 | |
| | | 100 | 14 | |
| 1-dodecylaza-cycloheptan-2-one | B | 25 | 0 | |
| | | 50 | 0 | |
| | | 100 | 0 | |
| 3-(3,4-dichloro-phenyl)-1,1-di-methylurea | C | 25 | 0 | |
| | | 50 | 0 | |
| | | 100 | 0 | |
| | A + B + C | 25 + 50 + 25 | 86 | (0) |
| Comparison | A + C | 50 + 50 | 71 | (10) |

EXAMPLE 6

Young cotton plants in the 6 to 7 leaf stage were treated as in Example 5 and evaluated after 3 weeks at unfavorable temperatures (mainly between 14° and 20° C.).

| Components of invention | | Rate in g/ha | Defoliation (%) | E (according to Colby) |
|---|---|---|---|---|
| 1-Phenyl-3-(1,2,3-thiadiazol-5-yl)-urea | A | 9 | 0 | |
| | | 20 | 0 | |
| | | 100 | 7 | |
| 1-dodecylaza-cycloheptan-2-one | B | 85 | 0 | |
| | | 500 | 0 | |
| 3-(3,4-dichloro-phenyl)-1,1-di-methylurea | C | 2 | 0 | |
| | | 20 | 0 | |
| | | 100 | 0 | |
| | A + B + C | 9 + 85 + 2 | 82 | (0) |
| Comparison | A + C | 20 + 20 | 64 | (0) |

EXAMPLE 7

Young cotton plants in the 6 leaf stage were treated with the active ingredients given below (repeated 4 times). The volume of spray used was 200 l/ha. A few days after application of the active ingredients, and maintaining at unfavorable temperatures (mainly between 12° and 20° C.), the percentage of discharged leaves was ascertained.

| Components of invention | | Rate in g/ha | Defoliation (%) | E (according to Colby) |
|---|---|---|---|---|
| 1-Phenyl-3-(1,2,3-thiadiazol-5-yl)-urea | A | 25 | 0 | |
| | | 50 | 0 | |
| | | 100 | 10 | |
| 1-dodecylaza-cycloheptan-2-one | B | 50 | 0 | |
| | | 100 | 0 | |
| | | 500 | 0 | |
| 3-(3,4-dichloro-phenyl)-1,1-di-methylurea | C | 5 | 0 | |
| | | 10 | 0 | |
| | | 12.5 | 0 | |
| | | 50 | 0 | |
| | | 300 | 0 | |
| | A + B + C | 25 + 50 + 5 | 24 | (0) |
| | A + B + C | 50 + 100 + 10 | 48 | (0) |
| | A + B + C | 25 + 200 + 12.5 | 68 | (0) |
| Comparison | A + C | 50 + 50 | 19 | (0) |

I claim:

1. Composition for defoliation of plants which is characterised by comprising a mixture of the components (A) one part of 1-phenyl-3-(1,2,3-thiadiazol-5-yl)urea and
(B) 1–100 parts of 1-dodecylazacycloheptan-2-one.

2. Composition according to claim 1 characterised in that it comprises for each part by weight of component A, 1 to 50 parts by weight of component B.

3. Composition according to claim 1 further containing up to 10 parts per part of A of 3-(3,4-dichlorophenyl)-1,1-dimethylurea.

4. Composition according to claim 3 characterised in that it comprises for each part by weight of component A, 1 to 50 parts by weight of component B and 0 to 5 parts by weight of component C.

5. Method for the defoliation of plants which comprises applying thereto an effective defoliation amount of the composition of claim 1.

6. Method according to claim 5 in which the plants are cotton plants and the composition is applied in an amount of 1 to 10,000 grams per hectare.

7. Method according to claim 6 in which the composition is applied in an amount of 100 to 2,000 grams per hectare.

8. Method according to claim 7 in which the composition contains 1 to 50 parts by weight of component B per part of component A.

9. Method for the defoliation of plants which comprises applying thereto an effective defoliation amount of the composition of claim 3.

10. Method according to claim 7 in which the composition contains 1 to 50 parts by weight of component B per part of component A and 0 to 5 parts by weight of component B.

11. Method according to claim 10 in which the plants are cotton plants and the composition is applied in an amount of 1 to 10,000 grams per hectare.

* * * * *